US012631632B1

(12) United States Patent
Mccullen et al.

(10) Patent No.: US 12,631,632 B1
(45) Date of Patent: May 19, 2026

(54) ASSAY TEST DEVICE AND METHOD

(71) Applicants: Nicholas Ross Mccullen, Brooklyn, NY (US); Marshall Ross Mccullen, Brooklyn, NY (US)

(72) Inventors: Nicholas Ross Mccullen, Brooklyn, NY (US); Marshall Ross Mccullen, Brooklyn, NY (US)

(73) Assignee: Nicholas McCullen, Brooklyn, NY (US)

(*) Notice: Subject to any disclaimer, the term of this patent is extended or adjusted under 35 U.S.C. 154(b) by 0 days.

(21) Appl. No.: 19/094,614

(22) Filed: Mar. 28, 2025

Related U.S. Application Data

(60) Provisional application No. 63/698,611, filed on Sep. 25, 2024.

(51) Int. Cl.
*G01N 33/543* (2006.01)
*G01N 33/50* (2006.01)
(Continued)

(52) U.S. Cl.
CPC ... *G01N 33/54388* (2021.08); *G01N 33/5002* (2013.01); *G01N 33/54346* (2013.01);
(Continued)

(58) Field of Classification Search
CPC ......... G01N 33/54388; G01N 33/5002; G01N 33/54346; G01N 33/553; G01N 33/68;
(Continued)

(56) References Cited

U.S. PATENT DOCUMENTS 5,354,692 A * 10/1994 Yang ............... G01N 33/54388
436/805
5,998,221 A * 12/1999 Malick ............ G01N 33/54388
435/7.1
(Continued)

FOREIGN PATENT DOCUMENTS

EP 1933147 A1 * 6/2008 ....... G01N 33/54388
WO WO-2005031356 A1 * 4/2005 ....... G01N 33/54389
(Continued)

OTHER PUBLICATIONS

Scarsi et al ("A multi-line platinum nanozyme-based lateral flow device for the colorimetric evaluation of total antioxidant capacity in different matrices", Nanoscale Advances, 2023, 5, 2167-2174) (Year: 2023).*

*Primary Examiner* — Christopher L Chin
(74) *Attorney, Agent, or Firm* — QuickPatents; Kevin Prince

(57) ABSTRACT

A rapid diagnostic device for detecting multiple biomarkers in bodily fluid samples, particularly useful for disease screening including breast cancer. The device comprises a housing containing at least one test strip with a sample receiving zone, conjugate pad, and multiple test zones. The test strip utilizes specific materials including Cytiva GF/DVA and Ahlstrom 1667 sample pads, an Ahlstrom 6613 conjugate pad with carboxylated 150 nm gold nanoshell conjugates, and a Sartorius CN140 membrane with precisely positioned test and control zones. The device simultaneously detects multiple biomarkers, such as hCG and CA-15-3, using specific antibodies. Features include a built-in safety lancet, integrated buffer system, and compatibility with various sample types. Results are available within ten minutes, with options for quantitative analysis via a dedicated reader or smartphone application. This multi-biomarker
(Continued)

approach potentially improves screening accuracy compared to single-marker tests, offering versatility for detecting various medical conditions.

20 Claims, 3 Drawing Sheets

(51) Int. Cl.
   *G01N 33/553*          (2006.01)
   *G01N 33/68*           (2006.01)
(52) U.S. Cl.
   CPC ........... *G01N 33/553* (2013.01); *G01N 33/68* (2013.01); *G01N 2333/59* (2013.01); *G01N 2800/365* (2013.01); *G01N 2800/7028* (2013.01)
(58) Field of Classification Search
   CPC ......... G01N 2333/59; G01N 2800/365; G01N 2800/7028; G01N 33/558; G01N 33/54387; G01N 33/54389; G01N 2021/7759; B01L 2300/0825
   USPC ....... 422/400, 401, 420, 421, 425, 426, 430; 435/7.23, 287.7, 287.9, 970, 805, 810; 436/64, 65, 169, 170, 510, 514, 518, 530, 436/810, 811, 813, 814
   See application file for complete search history.

(56)                References Cited

U.S. PATENT DOCUMENTS

| | | | | |
|---|---|---|---|---|
| 6,306,642 | B1 * | 10/2001 | Nelson ............. | G01N 33/54366 436/514 |
| 7,109,023 | B2 * | 9/2006 | Kang ............... | G01N 33/54388 436/805 |
| 7,129,053 | B1 * | 10/2006 | Reiter .................. | C07K 16/121 435/7.1 |
| 8,722,426 | B2 * | 5/2014 | Lambotte ......... | G01N 33/56983 436/805 |
| 10,725,031 | B1 * | 7/2020 | Barbosa ................ | B01L 3/5023 |
| 11,061,026 | B2 * | 7/2021 | Beckley ................ | G01N 33/76 |
| 2001/0023075 | A1 * | 9/2001 | Wong ................... | G01N 33/543 436/514 |
| 2012/0184462 | A1 * | 7/2012 | O'Farrell ......... | G01N 33/54388 506/15 |
| 2016/0266083 | A1 * | 9/2016 | Zhang ................ | G01N 33/5308 |
| 2018/0356405 | A1 * | 12/2018 | Chou ................. | G01N 21/6452 |

FOREIGN PATENT DOCUMENTS

| | | | | |
|---|---|---|---|---|
| WO | WO-2020176569 | A1 * | 9/2020 | ....... G01N 33/57488 |
| WO | WO-2022159524 | A1 * | 7/2022 | ............ B01L 3/5023 |

* cited by examiner

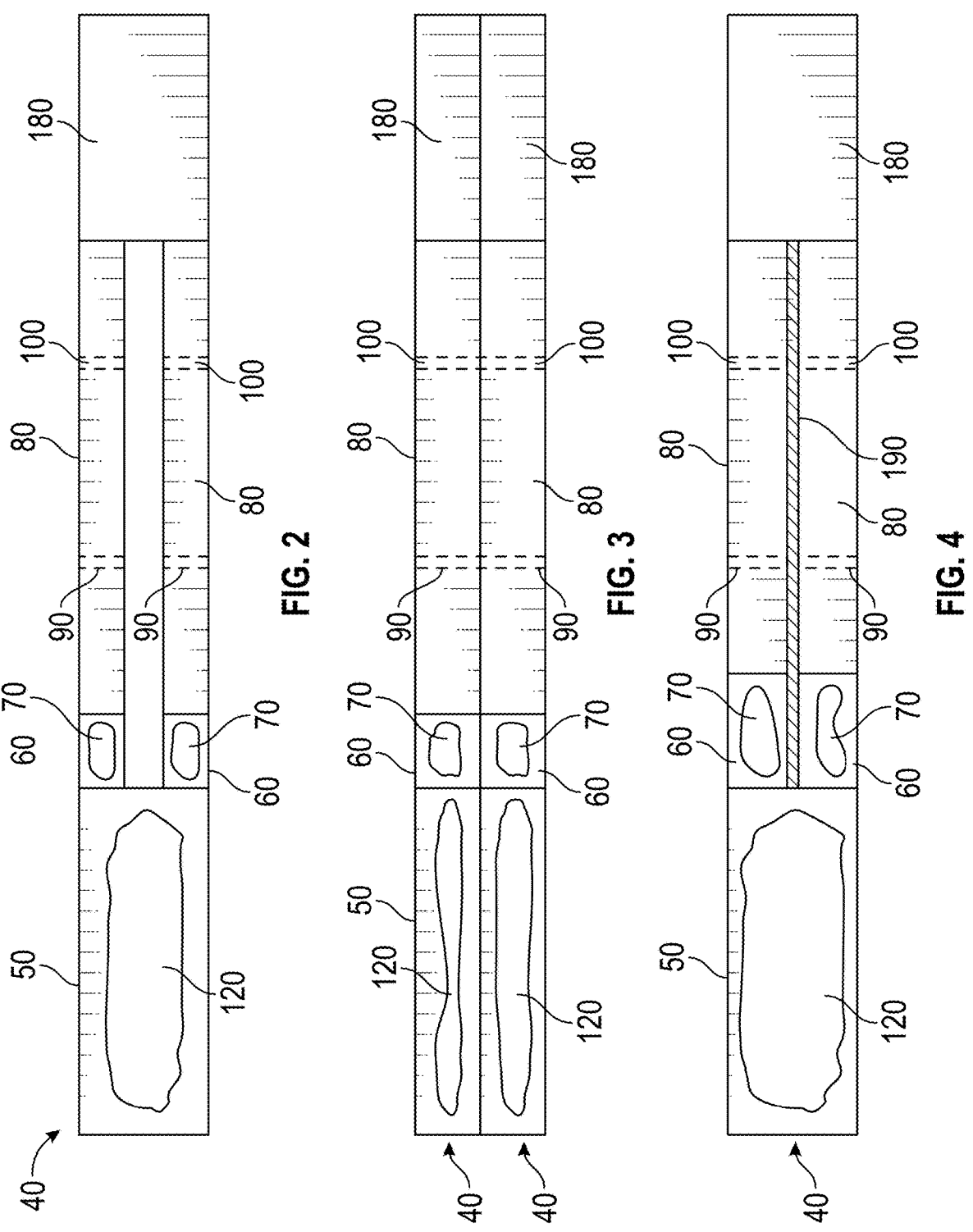

ASSAY TEST DEVICE AND METHOD

CROSS REFERENCE TO RELATED APPLICATIONS

This application claims the benefit of U.S. Provisional Patent Application 63/698,611, filed on Sep. 25, 2024, and incorporated herein by reference.

STATEMENT REGARDING FEDERALLY SPONSORED RESEARCH AND DEVELOPMENT

Not Applicable.

FIELD OF THE INVENTION

This invention relates to medical assay tests, and more particularly to a combination assay test for detecting medical conditions.

Early detection of various diseases, including different types of cancer and other medical conditions, is crucial for improving treatment outcomes and patient survival rates.

Traditional screening methods, while effective, often have limitations in terms of accessibility, cost, and potential for false results.

In recent years, there has been growing interest in the use of biomarkers for disease detection. Multiple biomarkers have been identified for various conditions, and their presence or elevated levels in bodily fluids can indicate the onset or progression of specific diseases. For instance, human chorionic gonadotropin (hCG) and cancer antigen 15-3 (CA-15-3) have both been associated with certain types of cancer, including breast cancer.

Lateral flow immunoassays have gained popularity as a rapid and cost-effective method for detecting various biomarkers. These tests are simple to use, provide quick results, and can be performed in a variety of settings, including at home or in point-of-care facilities. They have been successfully employed in pregnancy tests, infectious disease screening, and are increasingly being explored for other medical applications.

However, existing lateral flow tests often have limitations. Many tests focus on detecting a single biomarker, which can lead to reduced accuracy and increased likelihood of false results. Additionally, current devices may struggle with whole blood samples, requiring separate sample preparation steps. The sensitivity and specificity of these tests can also be inconsistent, potentially leading to missed diagnoses or unnecessary anxiety.

There is a clear need for a rapid diagnostic device that can simultaneously detect multiple biomarkers associated with various diseases in a single test. Such a device should be capable of handling whole blood samples directly, provide results quickly, and offer improved accuracy through the combined analysis of multiple biomarkers. Furthermore, an ideal device would be user-friendly, allowing for both professional use and at-home testing, with the option for quantitative analysis to aid in result interpretation. This type of innovation could significantly enhance screening efforts for multiple conditions, potentially leading to earlier detection and improved patient outcomes across a range of medical fields. The present invention accomplishes these objectives.

SUMMARY OF THE INVENTION

The present invention provides a rapid diagnostic device for detecting multiple biomarkers in a bodily fluid sample.

This device is particularly useful for screening various diseases and medical conditions, including but not limited to breast cancer. The device comprises a housing that contains at least one test strip, each with a sample receiving zone, conjugate pad, test zones, and a control zone.

The test strip utilizes a unique combination of materials and dimensions to optimize performance. The sample receiving zone includes two sample pads: a first pad made of Cytiva GF/DVA material and a second pad made of Ahlstrom 1667 material. These pads effectively separate plasma from whole blood samples with limited to no lysis of red blood cells. The conjugate pad, made of Ahlstrom 6613 material, contains dried particle conjugates specific to multiple biomarkers. These conjugates are carboxylated 150 nm gold nanoshells, coupled to antibodies via EDC/NHS coupling for enhanced sensitivity and specificity.

The test zones and control zone are located on a Sartorius CN140 membrane. Specific antibodies serve as immobilized capture reagents in the test zones, while a different antibody is used in the control zone. The precise positioning of these zones ensures clear result interpretation. An absorbent pad made of Ahlstrom 440 material is located at the end of the test strip, and all components are mounted on a backing card made of Kenosha material.

The device is designed to be user-friendly, with a built-in safety lancet for blood sample collection and an integrated buffer system for consistent sample preparation. It's compatible with various sample types including whole blood, serum, plasma, and urine, making it versatile for different testing scenarios.

Results are available within ten minutes, making the device suitable for rapid point-of-care testing. The device can be used with a dedicated reader for quantitative analysis or with a smartphone application for result capture and interpretation.

A key feature of this invention is its ability to simultaneously detect multiple biomarkers. A positive result for multiple markers can indicate a higher likelihood of specific conditions, potentially improving diagnostic accuracy compared to single-marker tests. In a specific embodiment, the device is configured to detect both hCG and CA-15-3, which when both positive, may indicate a higher likelihood of breast cancer.

The present invention addresses the drawbacks of the prior art by providing a rapid diagnostic device capable of simultaneously detecting multiple biomarkers in a single test. It handles whole blood samples directly, eliminating the need for separate sample preparation steps. The device offers improved accuracy through the combined analysis of multiple biomarkers, and its user-friendly design allows for both professional and at-home use. The option for quantitative analysis aids in result interpretation, potentially reducing false results and improving overall diagnostic reliability. This innovation represents a significant advancement in rapid, multi-biomarker testing for various medical conditions, offering potential for earlier detection and improved patient outcomes across multiple fields of medicine. Other features and advantages of the present invention will become apparent from the following more detailed description, taken in conjunction with the accompanying drawings, which illustrate, by way of example, the principles of the invention.

DESCRIPTION OF THE DRAWINGS

FIG. 2 is a top plan view of a test strip of an alternate embodiment, wherein a portion of the test strip is split into two separate conjugate pads and test zones;

FIG. 3 is a top plan view of a test strip of another alternate embodiment having two parallel and adjacent test strips;

FIG. 4 is a top plan view of a test strip of yet another alternate embodiment, similar to the embodiment of FIG. 2 but having a liquid impervious barrier between the conjugate pads and the test zones.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements, but can also mean a singular element.

Figure 1:
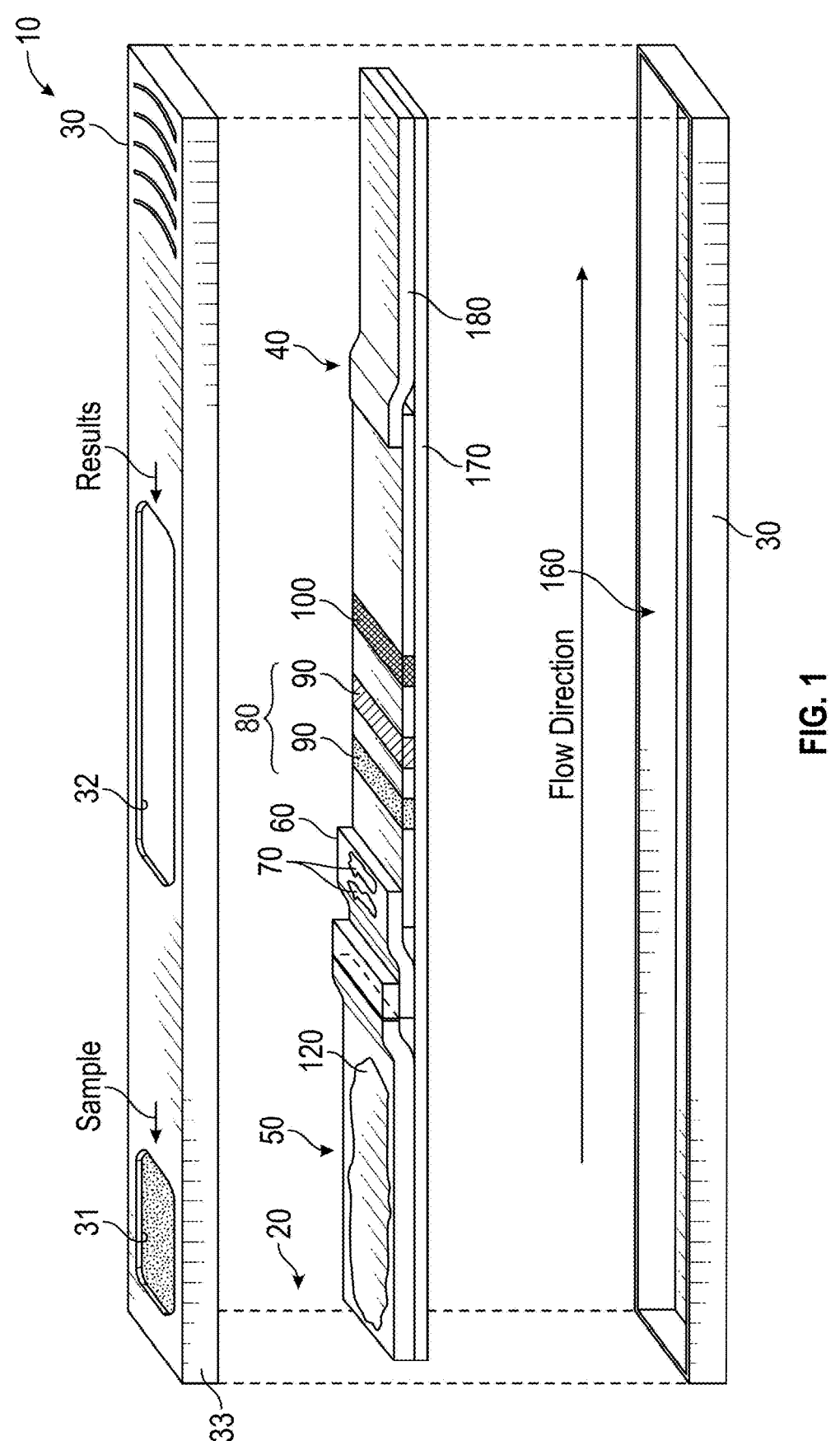
FIG. 1 is an exploded perspective view of one embodiment of the invention, illustrating a first embodiment having a single test strip with multiple test zones.

FIGS. 1 and 2 illustrate a rapid diagnostic device 10 for detecting multiple biomarkers in a bodily fluid sample 20. The rapid diagnostic device 10 comprises a housing 30 that encloses and protects internal components. The housing 30 may be made of plastic, biodegradable plastic, recycled materials, or the like.

Figure 5:
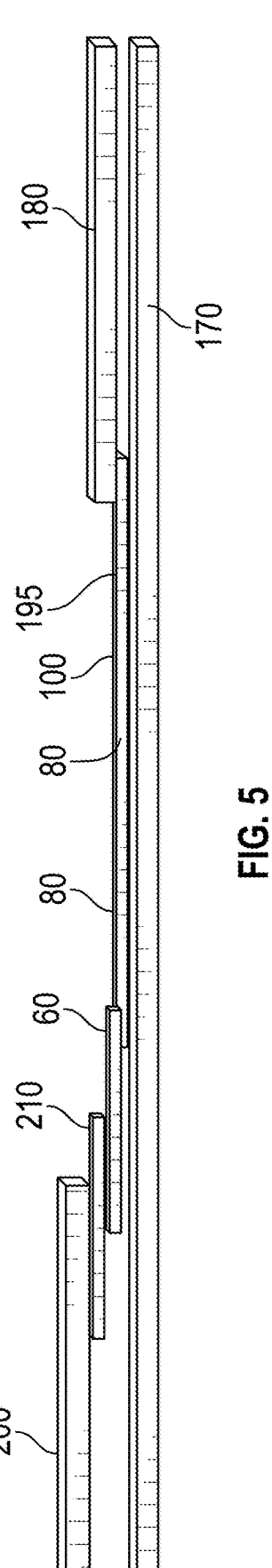
FIG. 5 is a perspective view of an alternate embodiment of the invention.

As shown in FIG. 5, the rapid diagnostic device 10 includes at least one test strip 40 disposed within the housing 30. Each test strip 40 comprises a sample receiving zone 50 at the first end configured to receive the bodily fluid sample 20. The sample receiving zone 50 includes a first sample pad 200 made of Cytiva GF/DVA material with a thickness of 0.682-0.834 mm and a length of 18-22 mm, and a second sample pad 210 made of Ahlstrom 1667 material with a thickness of 0.315-0.385 mm and a length of 9-11 mm.

Adjacent to the sample receiving zone 50 is a conjugate pad 60 containing dried particle conjugates 70 specific to at least two distinct biomarkers, such as hCG and CA-15-3. The conjugate pad 60 is made of Ahlstrom 6613 material with a thickness of 0.585-0.715 mm and a length of 9-11 mm. The conjugate pad 60 is a polyester fiber pad treated with buffering salt and surfactants to aid in hydrophilicity, nanoparticle conjugate stability, and rewetting.

The dried particle conjugates 70 comprise carboxylated 150 nm gold nanoshells conjugated to antibodies via EDC/

NHS coupling. This coupling method ensures efficient and stable attachment of the antibodies to the nanoparticles, enhancing the sensitivity and specificity of the test.

A liquid impervious barrier 190 is disposed between the conjugate pad 60 and the test zones 80. This barrier 190 is designed to inhibit cross-contamination between the conjugate pad 60 and the test zones 80, ensuring that the sample and conjugates flow in a controlled manner. The barrier 190 may be made of a hydrophobic material or a physical barrier that allows flow only through designated channels.

As illustrated in FIG. 3 and FIG. 5, each test strip 40 further includes at least two test zones 80 containing immobilized capture reagents 90 for detecting the distinct biomarkers, and a control zone 100 for indicating proper test function. These zones are located on a membrane 195 made of Sartorius CN140 material with a thickness between 0.216-0.297 mm and a length of 22.5-27.5 mm.

The first test zone 80 is located 6.75-8.25 mm (center) from the bottom edge of the membrane 195 with a width of 0.9-1.1 mm. The second test zone 80 is located 11.25-13.75 mm (center) from the bottom edge of the membrane 195 with a width of 0.9-1.1 mm. The control zone 100 is located 15.75-19.25 mm (center) from the bottom edge of the membrane 195 with a width of 0.9-1.1 mm.

The immobilized capture reagents 90 comprise Mouse anti-hCG antibodies in one test zone 80 and Mouse anti-CA15-3 antibodies in another test zone 80. The control zone 100 comprises Goat anti-Mouse antibodies.

An absorbent pad 180 is located at the end of the test strip 40, made of Ahlstrom 440 material with a thickness of 1.143-1.397 mm and a length of 21.6-26.4 mm. All components are mounted on a backing card 170 made of Kenosha material with a thickness of 0.229-0.279 mm and a length of 66.6-81.4 mm. The overall strip width is 3.6-4.4 mm.

The housing 30 includes an opening 31 at a first end 33 thereof that opens to the first end of each test strip 40. The opening 31 allows for introduction of the bodily fluid sample 20 into the device 10. The housing 30 also includes a viewing window 32 aligned with the test zones 80 and the control zone 100 of each test strip 40, allowing for visual inspection of test results.

The bodily fluid sample 20 flows along each test strip 40 from the sample receiving zone 50 through the conjugate pad 60 to the test zones 80 and control zone 100. This flow is facilitated by capillary action, ensuring proper sample distribution and interaction with the reagents. The device 10 is configured to detect multiple biomarkers simultaneously. A positive result on all test zones 80 indicates an overall positive test result for a specific medical condition, such as breast cancer when detecting both hCG and CA-15-3.

The rapid diagnostic device 10 may further comprise a built-in safety lancet (not shown) for collecting a blood sample. The safety lancet may be integrated into the housing 30 and designed to retract after use to prevent accidental injury. While not illustrated in the figures, this optional feature enhances the device's utility for at-home or point-of-care testing by providing a convenient and safe means of sample collection, and is readily understood by those skilled in the art.

In some embodiments, the sample receiving zone 50 includes an integrated buffer 120 for delivering a predetermined volume of buffer to the test strips 40. This system ensures consistent and appropriate buffer application, which is crucial for test accuracy.

The rapid diagnostic device 10 may be compatible with a point-of-care reader (not shown) for quantitative or semi-quantitative analysis of test results. The device 10 may also be used in conjunction with a mobile application for capturing and analyzing test results using a smartphone camera.

When the bodily fluid sample 20 is whole blood, the first sample pad 200 and second sample pad 210 act as whole blood retention sample pads, rapidly filtering plasma from whole blood. The red blood cells are retained in the pads with limited to no lysis, allowing only plasma (containing the biomarkers) to flow downstream.

The rapid diagnostic device 10 is configured to be compatible with multiple sample types including whole blood, serum, plasma, and urine. This versatility allows for broader application and user convenience.

To maintain the integrity of the test strips 40 and reagents, the rapid diagnostic device 10 includes a desiccant 160 within the housing 30 to maintain low humidity conditions.

The rapid diagnostic device 10 is designed to provide results within ten minutes or less after sample application, allowing for quick diagnosis and decision-making. This rapid result time, combined with the multi-biomarker detection capability, makes the device particularly suitable for point-of-care testing and home use scenarios.

The simultaneous detection of elevated levels of multiple biomarkers provides a stronger indication of specific medical conditions than single-marker tests, potentially improving the accuracy and reliability of the diagnosis.

In a preferred embodiment, the rapid diagnostic device 10 has the following specific dimensions and characteristics: The first sample pad 200 is made of Cytiva GF/DVA material with a thickness of 0.758 mm and a length of 20 mm. The second sample pad 210 is made of Ahlstrom 1667 material with a thickness of 0.35 mm and a length of 10 mm. The conjugate pad 60 is made of Ahlstrom 6613 material with a thickness of 0.65 mm and a length of 10 mm. The membrane 195 is made of Sartorius CN140 material with a thickness of 0.255 mm and a length of 25 mm. The absorbent pad 180 is made of Ahlstrom 440 material with a thickness of 1.27 mm and a length of 24 mm. All components are mounted on a backing card 170 made of Kenosha material with a thickness of 0.254 mm and a length of 74 mm. The overall strip width is exactly 4 mm. The first test zone 80 is located precisely 7.5 mm (center) from the bottom edge of the membrane 195, the second test zone 80 is at 12.5 mm (center), and the control zone 100 is at 17.5 mm (center), each with a width of 1 mm. The dried particle conjugates 70 are carboxylated 150 nm gold nanoshells. This precise configuration ensures optimal performance and reliability of the device for detecting multiple biomarkers.

While a particular form of the invention has been illustrated and described, it will be apparent that various modifications can be made without departing from the spirit and scope of the invention. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A rapid diagnostic device for detecting multiple biomarkers in a bodily fluid sample, comprising:
   a housing;
   at least one test strip disposed within the housing, each test strip comprising:
   a sample receiving zone at a first end configured to receive the bodily fluid sample,
   at least one conjugate pad containing dried particle conjugates specific to at least two distinct biomarkers,
   at least two test zones each containing immobilized capture reagents for detecting one of the distinct biomarkers,
   a control zone for indicating proper test function; and
   a barrier extending lengthwise along the at least one test strip, dividing the conjugate pad and the at least two test zones into two separate flow paths, wherein the conjugate pad includes labelled conjugates to two different analytes in each of the two separate flow paths;
   wherein the bodily fluid sample flows along each test strip from the sample receiving zone through the at least one conjugate pad to the test zones and control zone;
   wherein the at least one test strip is configured to detect at least two different biomarkers; and
   wherein a positive result in all test zones indicates an overall positive test result for a specific medical condition.

2. The rapid diagnostic device of claim 1, wherein the distinct biomarkers include hCG and CA-15-3.

3. The rapid diagnostic device of claim 1, wherein the housing includes an opening at a first end thereof that opens to the first end of the at least one test strip.

4. The rapid diagnostic device of claim 3, wherein the housing includes a viewing window aligned with the test zones and the control zone of the at least one test strip.

5. The rapid diagnostic device of claim 1, wherein the test zones are mutually adjacent.

6. The rapid diagnostic device of claim 1, wherein the sample receiving zone includes an integrated buffer for delivering a predetermined volume of buffer to the at least one test strip.

7. The rapid diagnostic device of claim 1, wherein the device is compatible with a point-of-care reader for quantitative or semi-quantitative analysis of test results.

8. The rapid diagnostic device of claim 1, further comprising a mobile application for capturing and analyzing test results using a smartphone camera.

9. The rapid diagnostic device of claim 1, wherein the bodily fluid sample is whole blood, and the device further comprises a blood separation membrane for separating plasma or serum from the whole blood sample.

10. The rapid diagnostic device of claim 1, wherein the device is configured to be compatible with multiple sample types selected from the group consisting of whole blood, serum, plasma, and urine.

11. The rapid diagnostic device of claim 1, wherein the dried particle conjugates comprise colloidal gold nanoparticles.

12. The rapid diagnostic device of claim 1, wherein the housing is made of a material selected from the group consisting of plastic, biodegradable plastic, and recycled materials.

13. The rapid diagnostic device of claim 1, further comprising a desiccant within the housing to maintain low humidity conditions for the at least one test strip.

14. The rapid diagnostic device of claim 1, wherein the sample receiving zone comprises a first sample pad made of Cytiva GF/DVA material and a second sample pad made of Ahlstrom 1667 material.

15. The rapid diagnostic device of claim 14, wherein the first sample pad has a thickness of 0.682-0.834 mm and a length of 18-22 mm, and the second sample pad has a thickness of 0.315-0.385 mm and a length of 9-11 mm.

16. The rapid diagnostic device of claim 1, wherein the at least one conjugate pad is made of Ahlstrom 6613 material with a thickness of 0.585-0.715 mm and a length of 9-11 mm.

17. The rapid diagnostic device of claim 1, wherein the test zones and control zone are located on a membrane made of Sartorius CN140 material with a thickness between 0.216-0.297 mm and a length of 22.5-27.5 mm.

18. The rapid diagnostic device of claim 1, further comprising an absorbent pad made of Ahlstrom 440 material with a thickness of 1.143-1.397 mm and a length of 21.6-26.4 mm.

19. The rapid diagnostic device of claim 1, wherein all components of the at least one test strip are mounted on a backing card with a thickness of 0.229-0.279 mm and a length of 66.6-81.4 mm.

20. The rapid diagnostic device of claim 1, wherein:

the sample receiving zone comprises a first sample pad made of Cytiva GF/DVA material and a second sample pad made of Ahlstrom 1667 material;

the at least one conjugate pad is made of Ahlstrom 6613 material;

the test zones and control zone are located on a membrane made of Sartorius CN140 material;

the device further comprises an absorbent pad made of Ahlstrom 440 material; and all components of the at least one test strip are mounted on a backing card.

* * * * *